United States Patent [19]

Baatz et al.

[11] 4,253,682
[45] Mar. 3, 1981

[54] PRESSURE-SENSITIVE COPYING PAPER SHEETS

[75] Inventors: Günther Baatz, Buxheim; Walter Schäfer, Cologne; Kurt Findeisen, Odenthal; Manfred Dahm, Leverkusen, all of Fed. Rep. of Germany

[73] Assignee: Bayer Aktiengesellschaft, Leverkusen, Fed. Rep. of Germany

[21] Appl. No.: 20,074

[22] Filed: Mar. 13, 1979

Related U.S. Application Data

[63] Continuation of Ser. No. 935,768, Aug. 22, 1978, abandoned.

[30] Foreign Application Priority Data

Aug. 26, 1977 [DE] Fed. Rep. of Germany ....... 2738509

[51] Int. Cl.$^3$ .................... B41M 5/16; B41M 5/22
[52] U.S. Cl. .................... 282/27.5; 252/316; 427/150; 427/151; 428/307; 428/537; 428/914
[58] Field of Search .................... 106/21; 252/316; 282/27.5; 427/150, 151; 428/307, 411, 537, 913, 914, 323, 327

[56] References Cited

U.S. PATENT DOCUMENTS

| 3,748,329 | 7/1973 | Liebsch et al. ............ 525/444 X |
| 4,021,595 | 5/1977 | Kiritani et al. ............ 428/307 |

FOREIGN PATENT DOCUMENTS 1670666 12/1970 Fed. Rep. of Germany .......... 282/27.5

*Primary Examiner*—Bruce H. Hess
*Attorney, Agent, or Firm*—Connolly and Hutz

[57] ABSTRACT

Pressure-sensitive copying paper containing a solution of a dye-precursor agent in microencapsulated form, wherein the dye-precursor agent is dissolved in a hydrophobic organic solvent and encapsulated in capsules composed of the polyaddition product of a diisocyanate of Formula (I)

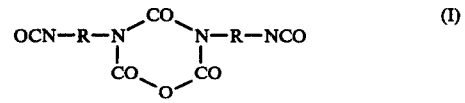

wherein R represents a divalent aliphatic radical, and a diamine.

1 Claim, No Drawings

PRESSURE-SENSITIVE COPYING PAPER SHEETS

This application is a continuation of application Ser. No. 935,768, filed Aug. 22, 1978, now abandoned.

The present invention relates to pressure-sensitive copying paper sheets comprising a colour-developing coating of microcapsules which contain as core material a solution of activatable dyestuff precursors and as their outer shell a polyaddition product from a diisocyanate having an oxadiazine trione structure and a diamine.

Pressure-sensitive copying papers are known (cf. M. Gutcho, Capsule Technology and Microencapsulation, Noyes Data Corporation 1972, pages 242–277; G. Baxter in Microencapsulation, Processes and Applications, published by J. E. Vandegaer, Plenum Press, New York, London, pages 127–143).

They are also described in U.S. Pat. No. 3,432,327. The term "pressure-sensitive copying papers" is used to describe papers in which two layers are in contact with each other, and each of which contains a dye-precursor component which reacts with the other to form a dyestuff. At least one of the dye-precursors is enclosed in microcapsules which are crushed by the pressure exerted with a writing tool and liberate the encapsulated component so that it can react with the second component. The two dye-precursor layers can be applied one on top of the other on one paper surface or separately on two contacting surfaces of paper.

According to U.S. Pat. No. 3,432,327 phase interface polymerisation—which is a polyreaction on the phase interface of a hydrophilic and a hydrophobic liquid—is employed for the production of microcapsules. The dye-forming reaction has to take place in a hydrophilic medium according to this U.S. patent. Therefore, a dye-precursor component is first dissolved in a hydrophilic liquid, e.g. water, and the first component of the capsule wall material is then added to this solution. The second component of the capsule wall material is dissolved in a hydrophobic liquid (oil, paraffin, aromatic solvent) and the hydrophilic solution is then dispersed in the hydrophobic liquid. The microcapsule is then formed from the two capsule wall components on the phase interfaces of the dispersed hydrophilic droplets.

The second dye-precursor component may also be encapsulated but is generally not.

Pairs of suitable dye-precursor components are listed in large numbers in the U.S. patent. They include pairs of inorganic salts (e.g., potassium hexacyanoferrate II/ammonium iron-(III)-sulphate), dyed metal complexes (e.g., diacetyldioxime/nickel acetate), and organic dyestuffs (e.g., bromine cresol purple/sodium hydroxide).

Capsule wall forming components are also listed in great numbers, e.g., the combination of specially selected diisocyanates and water, diol or diamine.

The mode of operation in U.S. Pat. No. 3,432,327 is directed towards the encapsulation of a solution of a dye-precursor agent in a hydrophilic solvent, preferably water. However, this has a great disadvantage as capsule walls which are impermeable to water cannot be obtained. These capsules are, therefore, not storage stable as they dry out after a relatively short time. Copying papers produced from them thus become unusable very rapidly.

The use of reaction products of diols or polyols having a molecular weight of from 400 to 10,000 and diisocyanates and polyisocyanates as isocyanate components in microencapsulation is known from German Offenlegungsschrift No. 23 11 712. According to this teaching, solutions of dyestuff precursors for copying papers can be encapsulated. The capsules thus obtained are, however, not impervious to the aromatic and alkyl aromatic solvents required for the process, though imperviousness is absolutely essential for good pressure-sensitive copying papers. Also, they have a very strong tendency to agglomerate. Agglomeration is disadvantageous in the production of pressure-sensitive copying papers because such capsules break already during production of the papers and a flawed paper is obtained. Under unfavourable conditions, the performance of the papers is substantially impaired.

Microcapsules for the production of copying papers have to meet several requirements:

1. The capsules must be impermeable to the dye-precursor agent and its solvent. Permeability to the dye-precursor agent causes discoloration, permeability to the solvent causes desiccating of the capsule content and thus ineffectiveness.

2. The capsules must only break under the pressure of writing instruments. The capsule walls must, therefore, resist other types of load.

3. The capsules must be at least predominantly individual particles and not large agglomerates.

4. The capsules must be easy to apply to the surface of the paper and be fixed immediately. Therefore, they must be stable to heat, so that they withstand drying up to 100° C.

It is also desirable to use as little shell material as possible and simultaneously to have capsule walls as impermeable as possible, in particular, to oxygen, and to the effects of light, and acid or bases.

The present invention is based on the fact that walls of microcapsules containing dye-precursor solutions for use in pressure-sensitive copying papers are obtained from diisocyanates of Formula (I)

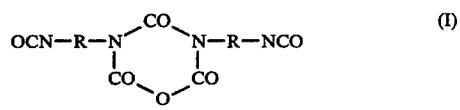

wherein B is a divalent aliphatic radical, preferably an alkylene radical having from 2 to 10 carbon atoms (wherein 1 or 2 carbon atoms can be replaced by oxygen), and a diamine. Capsule membranes which meet the above requirements are formed form the reaction product, in particular, if hydrophobic organic solutions of the dye-precursor agents are encapsulated.

The present invention provides a pressure-sensitive copying paper comprising a solution of a dye-precursor agent in microencapsulated form, wherein the dye-precursor agent is encapsulated as a solution in an organic solvent and the microcapsule walls are comprised of the polyaddition product of a diisocyanate of Formula (I)

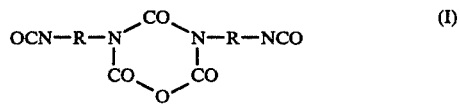

wherein R is a divalent aliphatic radical, optionally containing an oxygen atom, and a diamine.

The present invention also relates to the use of a solution of a dye-precursor agent in an organic solvent as core material in microcapsules whose walls are composed of the polyaddition product of a diisocyanate corresponding to Formula (I) and a diamine, for the production of pressure-sensitive copying papers. The diisocyanates corresponding to Formula (I) include derivatives of 2,4,6-triketo-1,3,5-oxadizines having two free isocyanate groups. Compounds in which the R radicals are derived from butane, hexane, octane and dodecane are particularly suitable. The n-hexane radical is preferred. The products and their preparation are known from German Auslegeschrift No. 1,670,666.

Suitable diamines include aliphatic primary or secondary diamines such as, for example, ethylene diamine-(1,2), bis(3-aminopropyl)-amine, hydrazine, hydrazineethanol-(2), Bis-(2)-methylaminoethyl)-methylamine, 1,4-diaminocyclohexane, 3-amino-1-methylaminopropane, N-hydroxyethyethylene diamine, N-methyl-bis-(3-aminopropyl)-amine, 1,4-diamino-n-butane, 1,6-diamino-n-hexane, ethylene-(1,2)-diamine-N-ethane-sulphonic acid (as alkali salt), 1-aminoethyl-ethylene diamine-(1,2), bis-(N,N'-amino ethyl)-ethylene diamine-(1,2). Dye-precursor agents are essentially colourless, basic products having various chromophoric groups. Examples include bis-(p-aminoaryl)-phthalides, leucoauramines, acylauramines, α,β-unsaturated aryl ketones, basic monoazo dye-stuffs, rhodamine-B-lactams such as N-(p-nitrophenyl)-rhodamine B-lactams, polyaryl carbinoles substituted by amino groups and their reaction products, for example, their esters or ethers and various heterocyclic spirans. Preferred compounds include 3,3-bis(p-dimethylamino phenyl)-6-diethylamino-phthalide (crystal violet lactone). Benzoylleucomethylene blue and derivatives of Michler's hydrol, in particular, the p-toluenesulphinate of Michler's hydrol.

Solvents for the basic dye-precursor components and for the diisocyanate are, generally, aromatic hydrocarbons which may also be substituted by alkyl or halogen.

Examples include chlorinated diphenyls, dodecyl benzene, mixtures of partially hydrated and non-hydrated terphenylene, isopropyl diphenyl, diisopropylbenzene, benzoic ethyl ester, mixtures of diphenyl and diphenyl ethers, phthalic acid dibutyl ester, aralkyl or diaryl ethers, the xylols of mixtures of aromates produced commercially in petrochemical and natural gas aromatization plants.

The solvent for the diamines is generally water.

When writing on the pressure-sensitive copying papers, the core material liberated by pressure contacts the receiver coating which develops dyestuffs from the colourless precursor, so that a copy of the writing appears. Coating materials include natural and synthetic products such as kaolin, attapulgite, montmorillonite, betonite, acidic Fuller's earth or phenol resins. Acid-activatable dyestuff precursors can be inserted, for example, in the microcapsule layer and acidic components can be in the receiver coating.

Microcapsules can be produced in various ways. For example, the diisocyanate and the dyestuff precursor can be dissolved in a suitable solvent and this organic phase be emulsified in an aqueous diamine solution which may optionally also contain protective colloids. It is also feasible to first emulsify the organic phase with or without surface-active agents and protective colloids in water up to a desired particle size, and then subsequently add the diamine required for forming the capsule wall to the aqueous phase.

Emulsifying agents can be added to the aqueous phase to emulsify and stabilize the emulsion formed. Examples of such products acting as protective colloids include carboxymethyl cellulose, gelatin and polyvinyl alcohol. Examples of emulsifiers include oxethylated, 3-benzyl-hydroxybiphenyl, reaction products of nonylphenol with various quantities of ethylene oxide and sorbitane fatty acid esters.

Polyaddition for forming the capsule walls can be controlled by way of the amine consumption. Upon completion of the reaction of the free isocyanate groups, the oxadazine ring of the isocyanate can be opened by raising the temperature so that a new isocyanate group is formed which then reacts with additional amine or with another under crosslinking and hardening of the polyaddition product.

The microcapsules can be produced continuously or discontinuously. Dispersion apparatus which produce a shear gradient are generally used. Examples include leaf-type, basket-type and rapid stirrers; colloid mills; homogenizers; ultrasonic dispersers; nozzles; jet nozzles and "Supraton" machines. The intensity of turbulence during mixing usually determines the diameter of the microcapsules obtained. Capsules of from 1 to 2000 microns can be produced. Capsules having diameters of from 2 to 20 microns are, however, preferred. The capsules do not agglomerate and have a narrow particle size distribution. The ratio by weight of the core material to the shell material is normally 50 to 90 to 50 to 10.

Pressure-sensitive copying papers are produced in known manner (cf. M. Gutcho, Capsule Technology and Microencapsulation, Noyes Data Corporation 1972, pages 242–277). The microcapsule suspensions obtained generally contain from 10 to 35% by weight of capsules. They tend to cream if they do not contain binder, but this may be exploited for raising the concentration. The most preferred capsule size is about 10 microns. The homogenized capsule suspensions provided with binders and optionally with inert fillers such as talc or kaolin can be applied to base paper, (e.g., from 40 to 100 g/m$^2$) either manually by means of a doctor blade or mechanically by means of an air brush, in quantities of from 4 to 8 g/m$^2$. Methods which can be used for coating base paper are described in German Offenlegungsschriften Nos. 1,934,457 and 1,995,542. The papers thus coated contain the first dye-precursor component, the "donor" component.

The "donor" component is, generally, on the reverse of the uppermost sheet in stacks of copying paper, and the front side of the next lower sheet is coated with the second dye precursor component, the "receiver" component. With stacks of copying paper, the "receiver" component is the upper side of the second sheet of paper. In the case of multiple stacks of copying paper, the successive, "donor" components must, of course, have a corresponding "receiver" component. The production of "receiver" components is known and is also described in the afore-mentioned German Offenlegungsschriften Nos. 1,934,457 and 1,955,542.

EXAMPLE 1

(a) Production of the wall-forming material 2000 g of n-hexane-1,6-diisocyanate are mixed in a 2.7 liter autoclave with 1 g of tri-p-tolylarsinic oxide and are stirred for 8 hours at a $CO_2$ pressure of 3 atmospheres at 50° C.

17.5 l of carbon dioxide are incorporated in this process. The reaction is stopped by addition of 2 g of phosphorus trichloride and the reaction product is separated from the unreacted starting products in a thin layer evaporator (two passages heating temperature 180° C. at 1 Torr).

1,957 g of oxadiazinone having an NCO value of 19.0% and a viscosity of 2,480 cp/50° C. are obtained. The IR spectrum displays the characteristic carbonyl absorption bands at 5.50 to 5.71 and 5.82 μm.

(b) Encapsulation 0.75 g of crystal violet lactone and 0.25 g of N-benzoyl-leucomethylene blue are dissolved in 25 g of solvent naphtha (mixture of aromatic substances made by BV Aral from xylene, cumene, toluene and other naphthene oils) with stirring and heating at 70° C.

After cooling of the solution, 5 g of the oxadiazinone (described in Example 1a) are added to the solution and dissolved.

The homogeneous organic phase is subsequently emulsified in 300 g of water containing 1.5 g of Mowiol 56-98 (polyvinyl-alcohol made by Hoechst AG), as emulsifying agent.

A Kotthoff mixing siren is used for emulsifying the mixture (8900 r.p.m., 1 beaker).

After emulsifying for about 1 minute, the mixing siren is replaced by a laboratory mixer of the Lenart Rapid type (500 r.p.m.). A solution of 0.7 g of 1-aminoethylethylene-diamine-1,2-(diethylenetriamine) in 70 g of water are simultaneously added to the mixture. The mixture is rapidly heated to 70° C. with continuous stirring and is kept at this temperature for about one hour. The heating phase merely serves for forming a shell which is as stable as possible. The diameter of the resulting microcapsules is of the order of from 3 to 25 μm.

EXAMPLE 2

The organic phase is prepared (as described in Example 1 b) with the modification that 25 g of Solvesso 200 (mixture of aromatic substances made by Esso AG) are used as solvent.

Encapsulation and subsequent treatment are carried out in the same manner (described in Example 1 b) with the modification that 0.7 g of ethylenediamine in 70 g of water are added to the external phase as amine component.

Microcapsules having a size of from 3 to 25 μm are produced.

EXAMPLE 3

0.75 g of p-toluene sulphinate of Michler's hydrol are dissolved in 25 g of phthalic acid-di-n-butyl ester as colour-giving component with stirring and heating at 80° C. After cooling the solution, 5 g of the oxadiazinone (described in Example 1 a) are added and dissolved. The resulting organic phase is encapsulated and further treated (as described in Example 1 b). 0.7 g of diethylene triamine in 70 g of water are used as the amine component. The resulting microcapsules have diameters of from 2 to 20 μm.

EXAMPLE 4

(a) Production of the wall-forming material.

280 g of 1,4-tetramethylene-diisocyanate are saturated by the introduction of dry $CO_2$ gas and mixed with 0.7 g of tri-n-butyl-phosphine (0.25%) with stirring and further introduction of carbon dioxide at 60° C. After two hours, the NCO value has dropped to 53.8%. The reaction mixture is separated in a thin-layer evaporator (heating temperature 180° C. at 1 Torr), so that 219 g of 1,4-tetramethylene-diisocyanate are recovered and 54 g of a viscous oil are obtained. This oil displays bands which are characteristic of isocyanate group-containing oxadiazine triones in the IR spectrum (4,4; 5,48; 5,71; 5,83; 6,93; 7,0.6 μm) and has an NCO value of 20.2% and a molecular weight of 375.

(b) Encapsulation 1.1 g of crystal violet lactone are added to 25 g of a mixture composed of 70 parts of Santosol 340 (partially hydrated terphenyl made by the firm Monsanto) and 30 parts of Solvesso 200 (mixture of aromatic substances made by Esso AG) at a temperature of 80° C. with stirring.

After cooling the solution, 5 g of the oxadiazinone (described under 4 a) are added and dissolved. The solution which represents the organic phase is subsequently emulsified in 150 g of water containing 0.75% of Mowiol 26-88 (polyvinylalcohol made by Hoeschst AG) as emulsifying agent. A Kotthoff mixing siren is used for emulsifying (8900 r.p.m., 500 ml beaker, stirring time about 1 minute). After emulsification, a solution of 0.9 g of 1-aminoethyl-ethylene diamine-1,2(diethylene triamine) in 50 g of water are added to the mixture and the mixing siren is subsequently replaced by a laboratory mixer of the Lenart Rapid type (500 r.p.m.). The subsequent mixing time amounts to one hour at 60° C. The microcapsules produced have a diameter of 1 to 35 /μm.

EXAMPLE 5

A microcapsule dispersion having a capsule content of about 30% may be produced with the aid of an ultrasonic homogenizer (Minisonic type made by the firm Ultrasonics) with a solution of 4.5 parts of crystal violet lactone and 17 parts of the oxadiazinone (described under Example 1 b) in 75 parts of Santosol 340 (partially hydrated terphenyl made by the firm Monsanto) and 25 parts of Solvesso 100 (Esso AG) as organic phase.

150 parts of the organic phase to 250 parts of aqueous phase are used for emulsification. The aqueous phase contains 0.5% of Mowiol 26-88 and 0.1% of Tween 80 (emulsifier made by the firm Atlas Chemie) as emulsifying agent.

The two phases and the emulsion obtained therefrom are passed 5 times through the ultrasonic homogenizer. The resulting emulsion is transferred to a beaker immediately afterwards and continuously mixed with a quantity of ethylene diamine (as an aqueous 4% solution) stoichiometrically corresponding to the NCO value of the oxadiazinone used, with stirring by means of a laboratory stirrer (Lenart Rapid type, 500 r.p.m.). The microcapsule dispersion formed is subsequently stirred at room temperature for about one hour. The microcapsule obtained have diameters of from 1 to 30 /μm.

EXAMPLE 6

0.75 g of p-toluene sulphinate of Michler's hydrol are dissolved in 25 g of benzoioethylester with stirring and heating at 80° C. After cooling the mixture, 5 g of the oxadiazinone (described in Example 1 a) are added and dissolved.

The resulting organic phase is emulsified with the aid of a Kotthoff mixing siren at 8900 r.p.m. in 300 g of water which contains 0.5% of Mowiol 56–98 as emulsifying agent.

After a mixing time of approx. 40 secs. a solution of 0.7 g of diethylene triamine in 70 g of water is added to the mixture. After 1 min. of emulsifying the mixing siren is replaced by a laboratory mixer (of the Lenart Rapid type, 500 r.p.m.) and the microcapsule dispersion is stirred for about one hour at 70° C.

The microcapsules have a diameter of 3 to 25 /μm.

What we claim is:

1. A pressure-sensitive copying paper comprising a solution of a dye-precursor agent in microencapsulated form, wherein the dyeprecursor agent is encapsulated as a solution in a hydrophobic organic solvent in microcapsules comprised of the polyaddition product of a diamine and a diisocyanate of formula

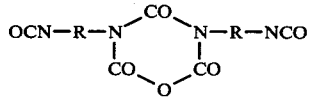

wherein R is n-hexylene.